US012575885B2

(12) United States Patent (10) Patent No.: US 12,575,885 B2
Liu et al. (45) Date of Patent: Mar. 17, 2026

(54) AUGMENTED REALITY GUIDANCE SYSTEM FOR CARDIAC INTERVENTIONAL SURGERY

(71) Applicant: Cornell University, Ithaca, NY (US)

(72) Inventors: Jun Liu, New York, NY (US); Bobak Mosadegh, New York, NY (US); Gurpreet Singh, Harrison, NJ (US); Simon Dunham, New York, NY (US); James K. Min, Brooklyn, NY (US); Subhi Al'Aref, New York, NY (US)

(73) Assignee: Cornell University, Ithaca, NY (US)

( * ) Notice: Subject to any disclaimer, the term of this patent is extended or adjusted under 35 U.S.C. 154(b) by 501 days.

(21) Appl. No.: 16/975,636

(22) PCT Filed: Feb. 26, 2019

(86) PCT No.: PCT/US2019/019592
§ 371 (c)(1),
(2) Date: Aug. 25, 2020

(87) PCT Pub. No.: WO2019/165430
PCT Pub. Date: Aug. 29, 2019

(65) Prior Publication Data
US 2020/0405397 A1 Dec. 31, 2020

Related U.S. Application Data

(60) Provisional application No. 62/635,222, filed on Feb. 26, 2018.

(51) Int. Cl.
*A61B 34/10* (2016.01)
*A61B 34/20* (2016.01)
*A61B 90/00* (2016.01)

(52) U.S. Cl.
CPC .............. *A61B 34/10* (2016.02); *A61B 34/20* (2016.02); *A61B 90/37* (2016.02); *A61B 90/39* (2016.02);
(Continued)

(58) Field of Classification Search
CPC ......... A61B 34/10; A61B 34/20; A61B 90/37; A61B 90/39; A61B 2034/102;
(Continued)

(56) References Cited

U.S. PATENT DOCUMENTS

| | | | |
|---|---|---|---|
| 9,721,379 B2 | 8/2017 | Zino et al. | |
| 2006/0241369 A1* | 10/2006 | Lienard .................. | A61B 90/37 |
| | | | 600/407 |

(Continued)

FOREIGN PATENT DOCUMENTS

KR 10-2018-0017005 A 2/2018

OTHER PUBLICATIONS

Fichtinger, Gabor et a l, Image overlay for CT-guided needle insertions, 1-24 Computer Aided Surgery, 2005, vol. 10, pp. 241-255 See the whole document.

(Continued)

*Primary Examiner* — John D Li
(74) *Attorney, Agent, or Firm* — FOLEY & LARDNER LLP

(57) ABSTRACT

The systems and method described herein can generate guidance images that can indicate the real-time position of a medical device within an anatomical target. For example, the images can be high-resolution, 3D holographic renderings of a catheter (an example medical device) within a patient's heart (an example anatomical target). The guidance system can generate images that include computer generated (CG) images or models of the medical device and target anatomy. The guidance system can generate the CG images (Continued)

of the target anatomy from pre-operative images of a first modality, such as CT images or MR images. The guidance system can determine real-time placement position of the medical device from an intra-operative image of a second modality, such as fluoroscopic images.

20 Claims, 11 Drawing Sheets

(52) U.S. Cl.
CPC ... *A61B 2034/102* (2016.02); *A61B 2034/105* (2016.02); *A61B 2034/107* (2016.02); *A61B 2090/367* (2016.02); *A61B 2090/3762* (2016.02); *A61B 2090/3966* (2016.02)

(58) Field of Classification Search
CPC ........ A61B 2034/105; A61B 2034/107; A61B 2090/367; A61B 2090/3762; A61B 2090/39; A61B 2090/66
See application file for complete search history.

(56)                    References Cited

U.S. PATENT DOCUMENTS

2008/0228065 A1*   9/2008   Viswanathan ........... A61B 5/06
                                                         600/426

2012/0265054 A1*   10/2012   Olson .................... A61B 34/20
                                                         600/424
2013/0058555 A1*   3/2013    Miao .................... G06V 20/653
                                                         382/132
2013/0279780 A1*   10/2013   Grbic .................. A61B 8/0883
                                                         382/131
2016/0157938 A1    6/2016    Breisacher et al.
2017/0209225 A1    7/2017    Wu
2017/0258418 A1*   9/2017    Averbuch ................. G06T 7/75
2017/0319165 A1*   11/2017   Averbuch .............. A61B 6/547
2017/0337682 A1*   11/2017   Liao .......................... G06T 7/30
2020/0375785 A1*   12/2020   Hansen ................ A61F 5/4404

OTHER PUBLICATIONS

Fichtinger, Gabor et a l, Image overlay for CT-guided needle insertions, 1-24 Computer Aided Surgery, 2005, vol. 10, pp. 241-255.
Foreign Action other than Search Report on PCT PCT/US2019/019592, dated Sep. 3, 2020.
International Search Report and Written Opinion in International Patent Application No. PCT/US2019/019592 dated Jun. 7, 2019 (11 pages).

* cited by examiner

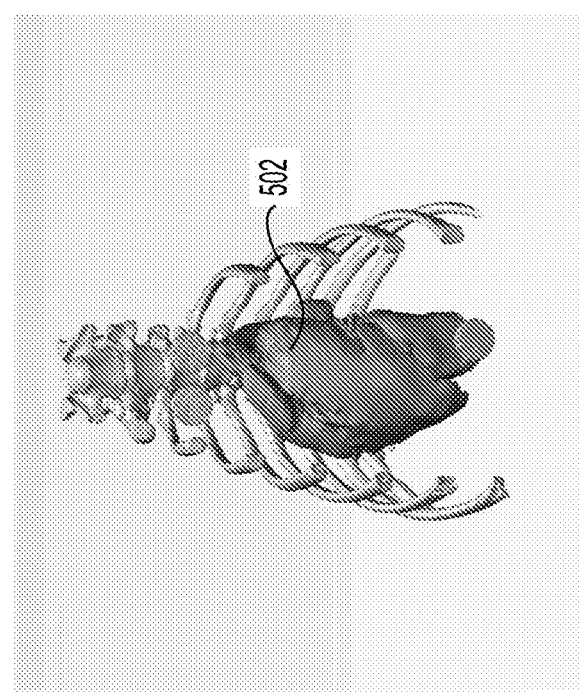
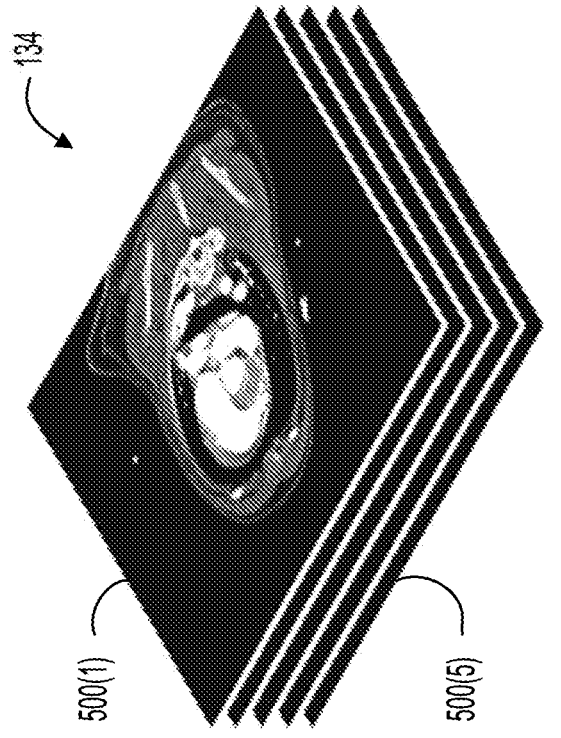
FIG. 5

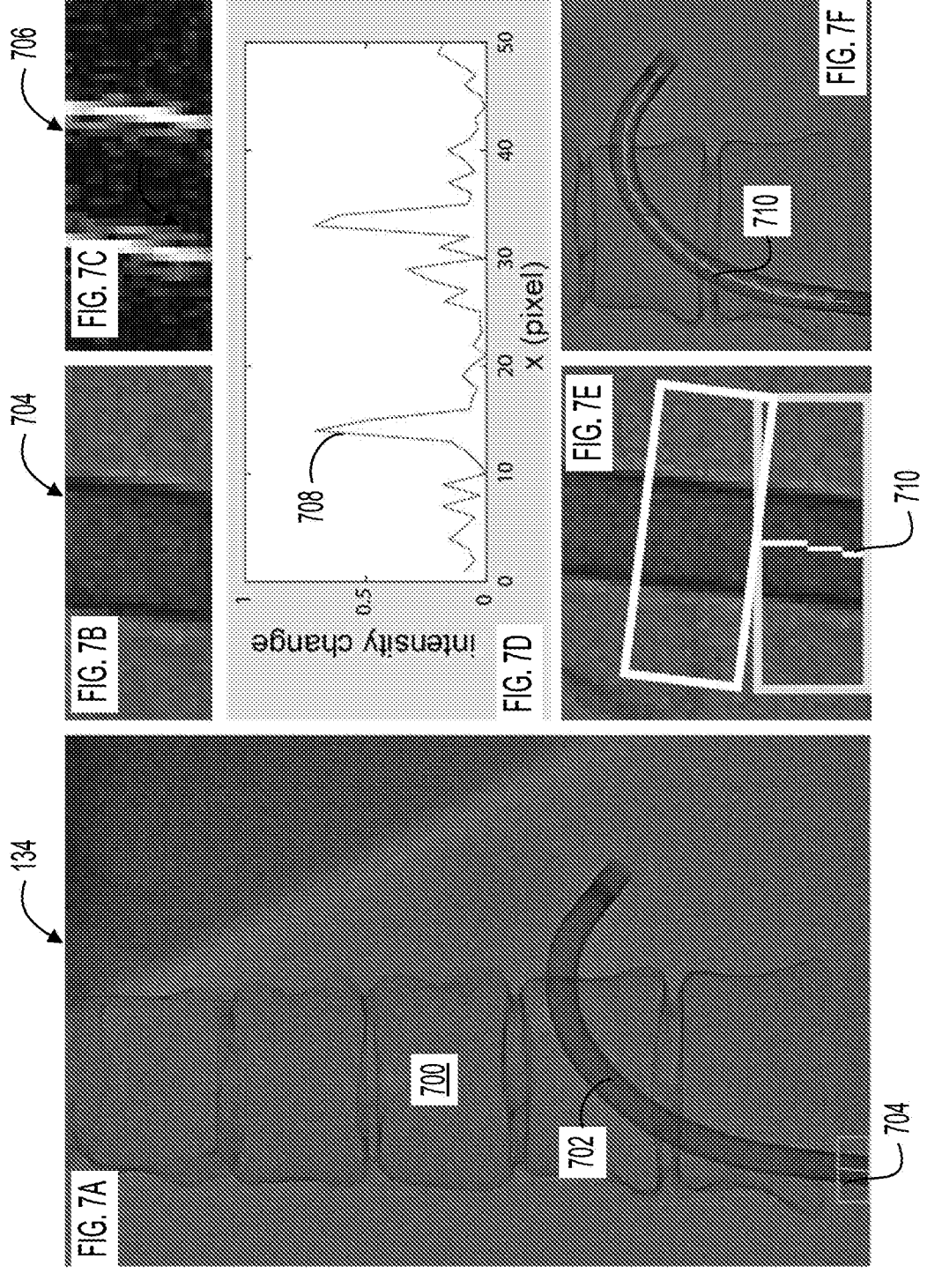

706

126

134

800

128

124

126

800

134

AUGMENTED REALITY GUIDANCE SYSTEM FOR CARDIAC INTERVENTIONAL SURGERY

CROSS REFERENCE TO RELATED APPLICATION

The present application is a U.S. National Stage Application under 35 U.S.C. § 371 of International Application No. PCT/US2019/019592, filed on Feb. 26, 2019, which claims priority to and the benefit of U.S. Provisional Patent Application No. 62/635,222, filed Feb. 26, 2018, which is herein incorporated by reference in entireties for all purposes.

BACKGROUND OF THE DISCLOSURE

Percutaneous cardiac interventions are these minimally invasive procedures that are used for a wide variety of cardiovascular ailments and are typically performed under imaging, such as X-ray fluoroscopy and echocardiography. The limitations of these imaging techniques increase the complexity of current procedures, which often require the interventionalist to determine the positioning of the catheter/ device by analyzing images from multiple imaging angles and modalities.

SUMMARY OF THE DISCLOSURE

According to at least on aspect of the disclosure, a method of image guidance can include receiving a first image data set that can include a spine of a subject and an anatomical target. The method can include generating a model of the anatomical target based on the first image data set and a model of the spine of the subject based on the first image data set in a first coordinate system. The method can include receiving at least one fluoroscopic image that can include the spine of the subject and a medical device. The method can include generating a mask of the spine from the at least one fluoroscopic image. The method can include generating a model of the medical device from the at least one fluoroscopic image in a second coordinate system. The method can include determining a transformation between the first coordinate system and the second coordinate system based on a registration of the model of the spine of the subject and the mask of the spine from the at least one fluoroscopic image. The method can include registering the model of the medical device with the with the model of the anatomical target based on the transformation between the first coordinate system and the second coordinate system. The method can include generating an image comprising the model of the medical device registered with the geometry of the anatomical target.

In some implementations, the first image data set can include pre-operative images of a first image modality different that fluoroscopy. The transformation can include at least one of a rotation angle, a translation, or a scaling factor. In some implementations, generating a mask of the spine from the at least one fluoroscopic image can include generating the mask of the spine with a convolutional neural network. The method can include generating a mask of the medical device from the at least one fluoroscopic image. Receiving the at least one fluoroscopic images can include receiving a first fluoroscopic image captured at a first angle and a second fluoroscopic image captured at a second angle. In some implementations, the output image is a three-dimensional (3D) model that can include the model of the medical device registered with the model of the anatomical target.

In some implementations, the first image data set can include computed tomography (CT) images or magnetic resonance (MR) images. The anatomical target can be the heart. The medical device can be a catheter. In some implementations, the catheter can include a radiopaque marker. In some implementations, determining the transformation can include determining at least one of a rotation angle, a translation, or a scaling factor based on a projection of the radiopaque marker in the at least one fluoroscopic image.

According to at least one aspect of the disclosure, a system for image guidance can receive a first image data set that can include a spine of a subject and an anatomical target. The system can generate a model of the anatomical target based on the first image data set and a model of the spine of the subject based on the first image data set in a first coordinate system. The system can receive at least one fluoroscopic image that can include the spine of the subject and a medical device. The system can generate a mask of the spine from the at least one fluoroscopic image. The system can generate a model of the medical device from the at least one fluoroscopic image in a second coordinate system. The system can determine a transformation between the first coordinate system and the second coordinate system based on a registration of the model of the spine of the subject and the mask of the spine from the at least one fluoroscopic image. The system can register the model of the medical device with the with the model of the anatomical target based on the transformation between the first coordinate system and the second coordinate system. The system can generate an image comprising the model of the medical device registered with the geometry of the anatomical target.

In some implementations, the first image data set can include pre-operative images of a first image modality different that fluoroscopy. The transformation can include at least one of a rotation angle, a translation, or a scaling factor. The system can generate the mask of the spine with a convolutional neural network. The system can generate a mask of the medical device from the at least one fluoroscopic image. The system can receive a first fluoroscopic image captured at a first angle and a second fluoroscopic image captured at a second angle. In some implementations, the output image is a three-dimensional (3D) model that can include the model of the medical device registered with the model of the anatomical target.

In some implementations, the first image data set can include computed tomography (CT) images or magnetic resonance (MR) images. The anatomical target can be the heart. The medical device can be a catheter. In some implementations, the catheter can include a radiopaque marker. In some implementations, the system can determine at least one of a rotation angle, a translation, or a scaling factor based on a projection of the radiopaque marker in the at least one fluoroscopic image.

The foregoing general description and the following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 5 illustrates the segmentation of image data sets to generate one or more models using the system illustrated in FIG. 1.

FIGS. 7A-7F illustrate the process for detecting the medical device in an image data set using the system illustrated in FIG. 1.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and method described herein can generate guidance images that can indicate the real-time position of a medical device within an anatomical target. For example, the images can be high-resolution, 3D holographic renderings of a catheter (an example medical device) within a patient's heart (an example anatomical target). The guidance system can generate images that include computer generated (CG) images or models of the medical device and target anatomy. The guidance system can generate the CG images of the target anatomy from pre-operative images of a first modality, such as CT images or MR images. The guidance system can determine real-time placement position of the medical device from an intra-operative image of a second modality, such as fluoroscopic images. Pre-operatively, the guidance system can segment the CT images, for example, to generate models of the anatomical target and at least one universal fiducial marker. The universal fiducial marker can be the spine. Intra-operatively, the guidance system can segment the fluoroscopic images, for example, to identify the universal fiducial marker and the medical device. The guidance system can identify the universal fiducial marker in the pre-operative images and the intra-operative images and use the universal fiducial marker to determine a transformation between the coordinate systems of the intra-operative images and the models generated from the pre-operative images. The guidance system can register the position of the medical device to the coordinate system of the models and generate one or more guidance image that indicates the real-time position of the medical device within the model of the anatomical target.

Figure 1:
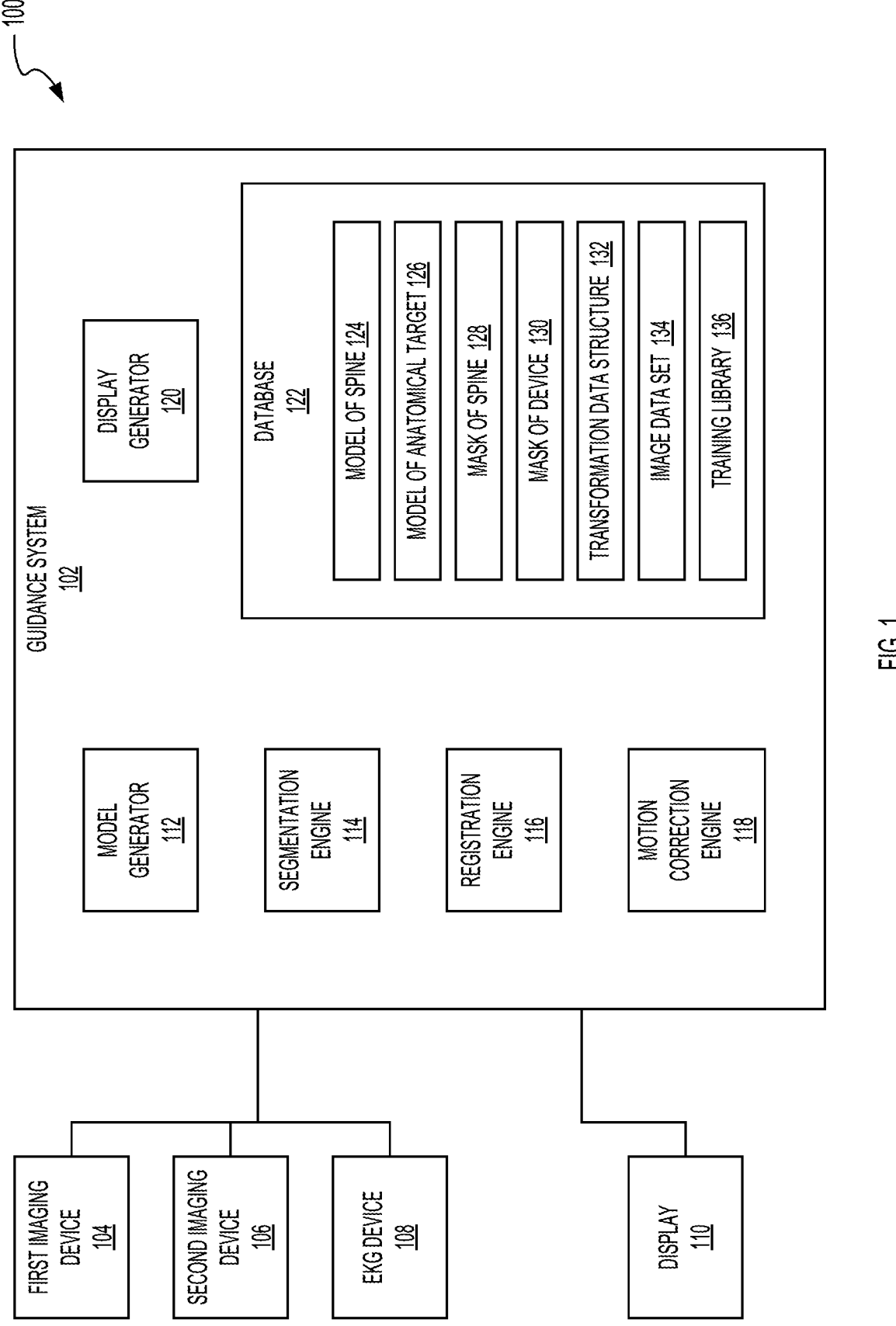
FIG. 1 illustrates an example system to guide the placement of medical devices.

FIG. 1 illustrates an example system 100 to guide the placement of medical devices. The system 100 can include a guidance system 102 that receives image data from a first imaging device 104 and second imaging device 106. The guidance system 102 can receive EKG data from an electrocardiogram (EKG) device 108. The guidance system 102 can generate guidance images can include models or images of a medical device co-registered, in real-time, with the models of anatomical targets. The guidance system 102 can transmit the guidance images to the display 110 for display to a user of the guidance system 102.

The guidance system 102 can include a model generator 112 to generate virtual models of the medical device, target anatomy, and fiducial markers. The guidance system 102 can include a segmentation engine 114 to segment the medical device, target anatomy, and fiducial markers from the background or other contents of imaging data. The registration engine 116 can include a registration engine 116 to co-register the image data from the first imaging device 104 with the second imaging device 106. The guidance system 102 can include a motion correction engine 118 to correct for motion artifacts that can be present in the imaging data. The motion artifacts can be generated by, for example, movement of the patient's heart. The guidance system 102 can include a guidance system 102 to generate and output an image that can include a co-registered virtual model of the medical device and target anatomy.

The system 100 can include a guidance system 102. The guidance system 102 can include at least one server or computer having at least one processor. For example, the guidance system 102 can include a plurality of servers located in at least one data center or server farm or the guidance system 102 can be a desktop computer, laptop computer, tablet computer, or other computing devices. The guidance system 102 can include a processor that can include a microprocessor, application-specific integrated circuit (ASIC), a field-programmable gate array (FPGA), other special purpose logic circuits, or combinations thereof.

The guidance system 102 can include a model generator 112. The model generator 112 can be an application, applet, script, service, daemon, routine, or other executable logic to generate computer models of the target anatomy or other components within image data, such as the universal fiducial marker. The model generator 112 can generate the models from image data sets 134. The generation of models by the model generator 112 is described further in relation to FIG. 5, among others. The model generator 112 can receive the image data sets 134 from the first imaging device 104 or the second imaging device 106. The first imaging device 104 can be a computed tomography (CT) device or a magnetic resonance (MR) imaging device. The model generator 112 can receive the image data sets 134 from the first imaging device 104 that include pre-operative images (e.g., CT images). For example, 1 week before an operation, the first imaging device 104 can capture CT images of the patient's heart. The CT images can include a universal fiducial marker, such as the patient's spine. The model generator 112 can receive the pre-operative images and generate the models before the operation involving the patient's heart.

The model generator 112 can generate models for one or more components within the image data sets 134. The models can be 3D, CG models. The model generator 112 can generate a model for the anatomical target based on the pre-operative image data sets 134. The anatomical target can be or can include the heart or other portion of the patient's vasculature. The model generator 112 can generate a model of the patient's spine based on the pre-operative image data sets 134. The guidance system 102 can use the spine as a universal fiducial marker.

The guidance system 102 can include a segmentation engine 114. The segmentation engine 114 can be an application, applet, script, service, daemon, routine, or other executable logic to segment image data from the image data sets 134 from the first imaging device 104 or the second imaging device 106. For example, the second imaging device 106 can be a fluoroscope and the segmentation engine 114 can segment fluoroscopic images. The segmentation engine 114 can segment the fluoroscopic images to segment or otherwise identify a universal fiducial marker (e.g., the subject's spine) and a medical device (e.g., a catheter). In some implementations, the segmentation engine 114 can segment the spine and medical device and generate a mask of the spine and medical device. The mask can be a bit mask. For example, the mask can be an image that includes 0's at locations in the fluoroscopic image that do not include the medical device or spine and 1's at locations in the fluoroscopic image that do include the medical device or the spine. In some implementations, the fluoroscope can transmit image data sets 134 to the guidance system 102 that can include a plurality of images captured at different angles. The segmentation engine 114 can segment each of the images captured at the different angles. The segmentation of the spine and medical device from the fluoroscopic image is described further in relation to FIGS. 6 and 7, among others. As described further below in relation to FIGS. 6 and 7, among others, the segmentation engine 114 can segment the images of the first and the second modalities using image processing to, for example, identify edges within the images. The segmentation engine 114 can identify objects within the images based on the identified edges. In some implementations, the segmentation engine 114 can use machine learning or computer vision to identify and segment objects from the image data sets 134. The segmentation engine 114 can include a convolutional neural network to identify the objects in the image data sets 134.

The guidance system 102 can include a registration engine 116. The registration engine 116 can be an application, applet, script, service, daemon, routine, or other executable logic to determining a transformation between the model of the universal fiducial marker generated from a first image data sets 134 from the first imaging device 104 (e.g., a CT device) and the universal fiducial marker segmented from the image data sets 134 of the second imaging device 106 (e.g., a fluoroscopic imaging device). The generating of the transformation is described further in relation to FIG. 8, among others.

The registration engine 116 can use the spine as a universal fiducial marker co-register the coordinate systems of models that the model generator 112 generates from the images of a first imaging modality (e.g., CT images) and the images of a second imaging modality (e.g., fluoroscopic images). For example, since the spine is a rigid object and has a relatively consistent position within the subject, the spine can be used as a universal fiducial marker. The registration engine 116 can generate a transformation that can include scaling factors, rotation factors, and translation factors that enable the guidance system 102 to place the spine and medical device as imaged by the first imaging device 104 and the second imaging device 106 within a single coordinate system. In some implementations, the transformation can be a transform matrix.

The guidance system 102 can include a motion correction engine 118. The motion correction engine 118 can be an application, applet, script, service, daemon, routine, or other executable logic to correct for motion artifacts. In some implementations, movement of the subject can introduce motion artifacts into the image data sets 134 generated by the first imaging device 104 or the second imaging device 106. The movement can include the movement of the subject's chest due to breathing or movement within the subject's chest due to the beating of the heart. The motion correction engine 118 can identify time points when the subject was in the same position of the breathing cycle or heartbeat to capture or analyze images from the first imaging device 104 and the second imaging device 106. In some implementations, the first imaging device 104 can be configured to capture pre-operative image data sets 134 during an inter-beat interval. For example, the first imaging device 104 can be coupled with an EKG device 108 to identify heartbeats and then capture the image data sets 134 between two consecutive heartbeats. The motion correction engine 118 can control the second imaging device 106 to capture image data sets 134 during the same portion of the heartbeat (e.g., the inter-beat interval) or can identify portions of the image data sets 134 captured during the same portion of the heartbeat as the image data sets 134 of the first imaging device 104. For example, the image data sets 134 generated by the second imaging device 106 can include a plurality of images sampled over a predetermined time to form a movie or series of images. The images can be time-locked with the signal from the EKG device 108. The motion correction engine 118 can identify, for example, an inter-beat interval between contractions of the subject's heart in the EKG signal and select the portions of the image data set 134 from the second imaging device 106 captured during the inter-beat interval.

The guidance system 102 can include a display generator 120. The display generator 120 can be an application, applet, script, service, daemon, routine, or other executable logic to generate virtual models that illustrate the real-time position of the medical device within the anatomical target. The display generator 120 can retrieve the transformation data structure 132 from the registration engine 116. The display generator 120 can register the geometry and position of the medical device with the with the model of the anatomical target based on the transformation to generate an image that includes the medical device's real-time position within the target anatomy. The display generator 120 can generate a 2D image that illustrates the real-time position of the medical device within the model of the anatomical target. The display generator 120 can generate a 3D image that illustrates the real-time position of the medical device within the model of the anatomical target. In some implementations, the display generator 120 can receive a user input to update the rotation, pan, zoom, or view of the 3D image. For example, the user can click and drag the displayed model of the anatomical target with a mouse to provide a different view of the 3D model of the anatomical target.

The guidance system 102 can include a database 122. The database 122 can be stored device memory or other suitable storage for computer program instructions and data. The memory can include all forms of non-volatile memory, media and memory devices, including semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry. As described above, the guidance system 102 can store model of the spines 124, the model of the targets 126, the mask of the spines 128, the mask of the devices 130, transformation data structures 132, transformation data structures 132, and a training library 136 in the database 122.

The model of the spine 124 and the model of the target 126 can be generally referred to as models. The models can be computer generated models. For example, the models can be computer-aided design (CAD) models that represent that anatomy of a subject. The models can be data structures that can include data indicating the 3D geometry and position of an object. For example, the data structure can be in an STL or other file format for storing 3D data. The mask of the spine 128 and the mask of the device 130 can generally be referred to as masks. The masks can be a data structure that indicates the location of an object (e.g., the spine or medical device) within, for example, a fluoroscopic image. The mask can be a matrix the same size as the fluoroscopic image that can include 0's at the position of the pixels in the fluoroscopic that do not include the object and 1's at the position of the pixels in the fluoroscopic that do include the object. The guidance system 102 can store transformation data structures 132 in the database 122. The transformation data structure 132 can be a data structure that includes a matrix of the scaling factors, rotation factors, and translation factors for transforming register the image data sets 134 from the first imaging device 104 with the image data sets 134 of the second imaging device 106. For example, the matrix can enable the location or coordinates of the spine in a fluoroscopic image (as identified by a mask of the spine 128) to be transformed into the coordinate system of the model of the spine 124. The guidance system 102 can store image data sets 134 in the database 122. The image data sets 134 can be images captured by the first imaging device 104 or the second imaging device 106. The image data sets 134 can be CT images, MR images, fluoroscopic images, or other types of image data.

The database 122 can include a training library 136. As described above, the segmentation engine 114 and the registration engine 116 can include a machine learning module, such as a convolutional neural network. The training library 136 can include training data for training the machine learning modules of the segmentation engine 114 and the registration engine 116. For example, the training library 136 can include image data sets 134 that are pre-segmented or include masks to identify the objects within the training data. The training library 136 can include pre-segmented fluoroscopic images, pre-segmented CT images, and pre-segmented MR images.

The system 100 can include a first imaging device 104. The first imaging device 104 can be a medical imaging device to capture pre-operative images of the subject and the subject's anatomy. For example, the first imaging device 104 can capture pre-operative images of the patient's heart and spine. The first imaging device 104 can be a medical imaging device capable of capturing 3D images of the subject. For example, the first imaging device 104 can capture a plurality of images (or "slices") along an axis of the subject. The plurality of slices can be stitched together to form a 3D volume. The first imaging device 104 can be a CT imager or an MR imager, for example. The first imaging device 104 can capture images that are provided to the guidance system 102 as image data sets 134.

The system 100 can include a second imaging device 106. The second imaging device 106 can be an imaging device that has a different imaging modality than the first imaging device 104. For example, the second imaging device 106 can be a fluoroscopic or echocardiographic imaging device. The second imaging device 106 can capture images that are provided to the guidance system 102 as image data sets 134. The second imaging device 106 can capture intra-operative images of the patient. The intra-operative images can include the spine and the medical device (e.g., a catheter). In some implementations, the second imaging device 106 captures 2D images. The image data sets 134 from the second imaging device 106 can include metadata. In some implementations, the fluoroscopic imaging device can be mounted on a C-arm such that the fluoroscopic imaging device can capture images from a plurality of different angles. The metadata can include an indication of the angle at the fluoroscopic imaging device captured the image.

The system 100 can include a display 110. The guidance system 102 can display the generated models to the user via the display 110. The display 110 can include on displays. The display 110 can be a cathode ray tube (CRT), a flat-panel device such as a liquid crystal display (LCD), a projection device, or some other mechanism for creating a visible image. In some implementations, the display 110 can be or can include an augmented reality system. For example, the display 110 can be integrated into glasses or other wearables with an integrated computing device. The display 110 can generate images overlaid on the user's field of view.

Figure 2B:
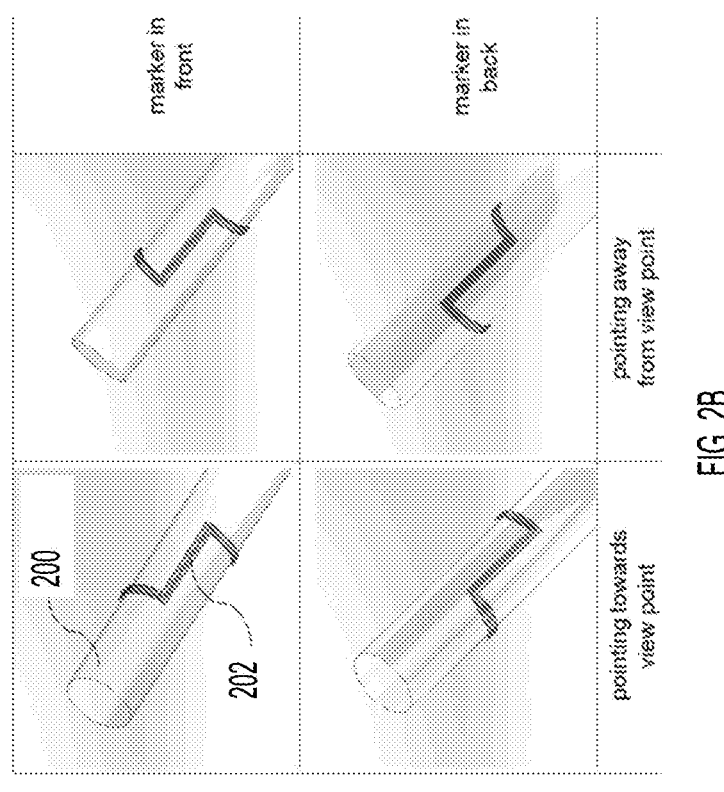
FIGS. 2A and 2B illustrate an example of catheter that can be used with the system illustrated in FIG. 1.
Figure 2A:
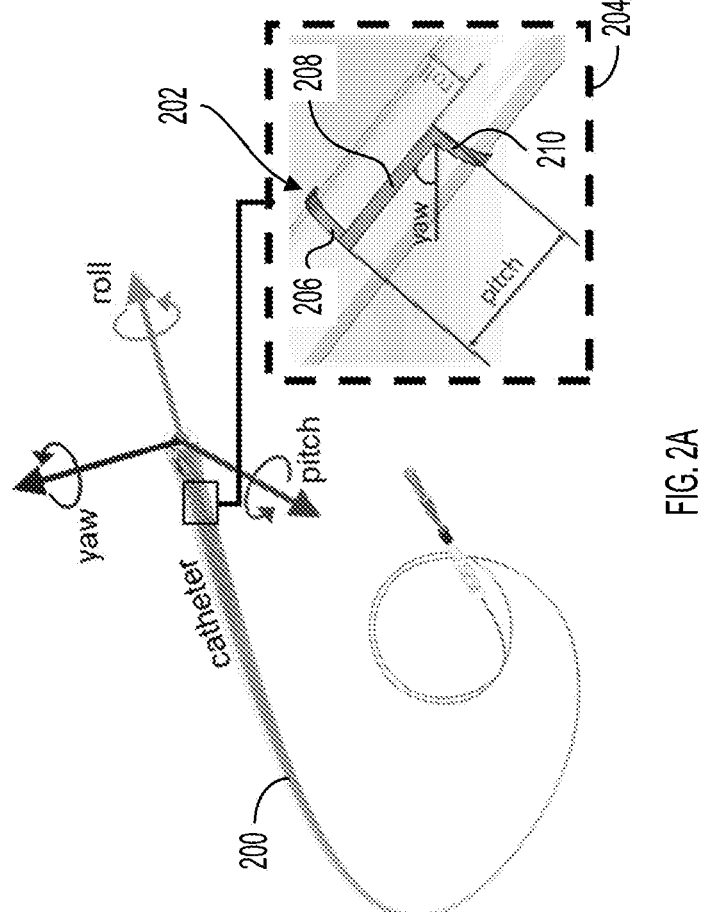

FIGS. 2A and 2B illustrate an example of catheter 200, which can be an example medical device used in the system 100 illustrated in FIG. 1. FIG. 2A illustrates the catheter 200 and the insert 204 illustrates an enlarged portion of the distal tip of the catheter 200. The catheter 200 can be used for the percutaneous introduction of medical devices, such as cardiovascular catheters to the heart for the delivery of, for example, cardiac leads. The catheter 200 can be a steerable guiding sheath. For example, the catheter 200 can be coupled with a handpiece that enables a user to control the movement (e.g., deflection) of the tip of the catheter 200. During the movement of the catheter 200 through the vasculature of the subject toward the target anatomy, the catheter 200 can roll about its longitudinal axis, pitch, or yaw.

The catheter 200 can have an outer diameter of between about 2 mm and about 7 mm, between about 2 mm and about 6 mm, between about 2 mm and about 5 mm, between about 2 mm and about 4 mm, or between about 2 mm and about 3 mm. The catheter 200 can taper along the length of the catheter 200. For example, the distal tip of the catheter 200 can have a smaller diameter when compared to the proximal end of the catheter 200, near the handpiece.

The catheter 200 can include a radiopaque marker 202. The radiopaque marker 202 can be coupled toward the distal tip of the catheter 200. The radiopaque marker 202 can include a material that can be detected or visualized in a fluoroscopic image to enable the catheter 200 to be visualized in situ. For example, the radiopaque marker 202 can include a metal or barium sulfate strip. The catheter 200 can enable the guidance system 102 to determine the 3D position of the catheter 200 using a single fluoroscopic image rather than two fluoroscopic images. The radiopaque marker 202 can encircle a circumference of the catheter 200. For example, the radiopaque marker 202 can include a plurality of radiopaque rings encircling the circumference of the catheter 200. As illustrated in FIGS. 2A and 2B, the radiopaque marker 202 can include a plurality of parallel line segments that meet at one or more angles. For example, the radiopaque marker 202 can include a first line segment 206 that at least partially encircles the circumference of the catheter 200 at a first longitudinal position, a second line segment 210 that at least partially encircles the circumference of the catheter 200 at a second longitudinal position, and a third and fourth line segments 208 that couples the first line segment 206 with the second line segment 210. As illustrated in FIG. 2A, the first line segment 206 and the second line segment can particularly encircle opposite halves of the catheter's circumference and the third and fourth lines segments 208 can form a 90° angle with the first line segment 206 and the second line segment 210. The line segments 208 can meet with the first line segment 206 and the second line segment 210 at between about 45° and about 135°, between about 65° and about 115°, or between about 80° and about 105°. FIG. 2B illustrates the radiopaque marker 202 at different rotational views. As described further in relation to FIGS. 3A-3B, when imaged with a 2D imaging system (e.g., a fluoroscopic imaging device), the radiopaque marker 202 is projected onto a 2D image plane. The guidance system 102 can measure the segments of the radiopaque marker 202 in the image plane to determine the position and orientation of the catheter 200 in a 3D volume.

Figures 3A, 3B:
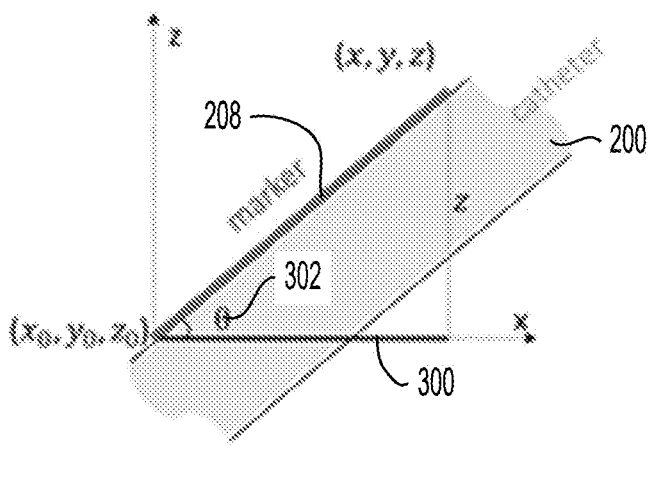
FIGS. 3A-3C illustrate various views of a catheter and radiopaque marker that can be used with the system illustrated in FIG. 1.
Figure 3C:
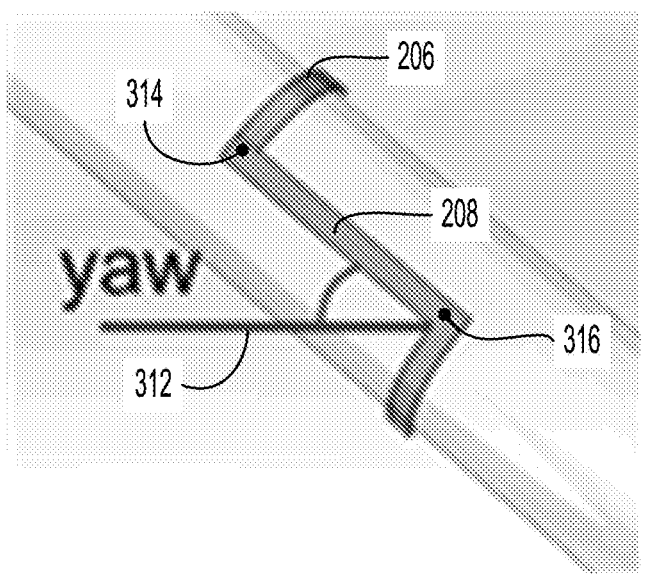

FIGS. 3A-3C illustrate various views of the catheter 200 and radiopaque marker 202. FIG. 3A illustrates a lengthwise cross-sectional view of the catheter 200 to illustrate the calculation of the out-of-plane angle (e.g., pitch angle) of the catheter 200. Imaging the catheter 200 projects the radiopaque marker 202 onto the image plane 300. The guidance system 102 can measure the length of the fourth line segment 208 in the image plane 300 to determine the pitch angle 302 of the catheter 200. For example, the pitch angle 302 can be calculated as θ=arccos((length of the line segment 208 in image plane 300)/(actual length of the line segment 208)).

FIG. 3B illustrates a cross-sectional view of the catheter 200 to illustrate the calculation of the roll of the catheter 200. The guidance system 102 can calculate the roll of the catheter 200 based on the distance 304 between the line segment 208 and the center line 306 of the catheter 200 and based on the radius 308 of the catheter 200. For example, the angle 310 of the roll is arcsin((distance 304)/(radium 308)).

FIG. 3C illustrates a side view of the catheter 200 to illustrate the calculation of the yaw angle 312. The yaw angle 312 can be based on the projected length of the line segment 208. For example, the yaw angle 312 can be based on the distance between a first endpoint 314 of the line segment 208 and a second endpoint 316 of the line segment 208. For example, the yaw angle 312 can be calculated as arctan((y−y_o)/(x−x_o)).

Figure 4:
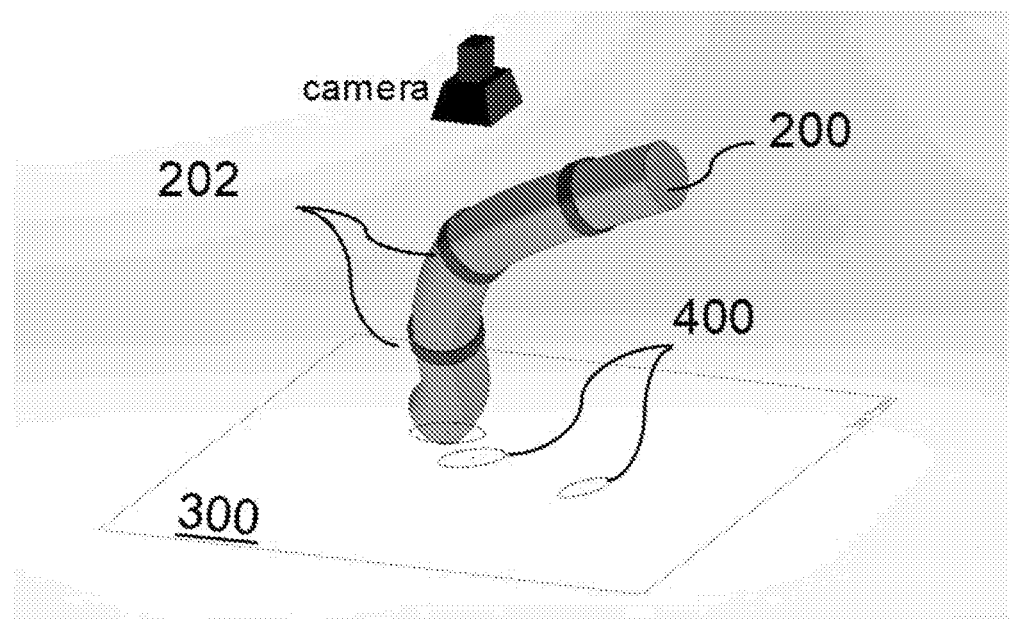
FIG. 4 illustrates an example catheter with radiopaque markers that can be used with the system illustrated in FIG. 1.

FIG. 4 illustrates an example catheter 200 with radiopaque markers 202. The example catheter 200 illustrated in FIG. 4 includes a plurality of radiopaque markers 202 configured as ring radiopaque markers. When imaged, the radiopaque markers 202 are projected onto the image plane 300 as projections 400. The guidance system 102 can determine the position of the guidance system 102 based on the position of the projections 400 on the image plane 300, the size of the projections 400 on the image plane 300, and the circularness (as defined by a ratio of the projections height to width). For example, given a catheter 200 with a circular cross-section, if the projection 400 is substantially circular (e.g., the height is equal to the width), the guidance system 102 can determine that the portion of the catheter 200 that contains the radiopaque marker 202 forming the circular projection 400 is pointing away from the image plane 300. For the example catheter 200, if the projection 400 is substantially a line (e.g., the projection 400 has a width but substantially no height), the guidance system 102 can determine that the portion of the catheter 200 that contain the radiopaque marker 202 forming the projection 400 is substantially parallel with the image plane 300.

FIG. 5 illustrates the segmentation of image data sets 134 to generate one or more models 502. The guidance system 102 can receive one or more image data sets 134 from the first imaging device 104 to generate the models 502. The model of the spine 124 and the model of the target 126 can be examples of the models 502. The model generator 112 can generate the models 502 from image data sets 134 received from the first imaging device 104, which can be a CT imager or MR imager. The image data sets 134 from the first imaging device 104 can be a volumetric image and can include a plurality of slices 500. For example, the image data set 134 includes the slices 500(1) to 500(4).

The model generator 112 can generate the models of the patient's anatomical structures by segmenting the image data sets 134. The model generator 112 can segment the image data sets 134 to identify portions of the image data sets 134 that belong to an anatomical structure and portions of the image data sets 134 that do not belong to the anatomical structure. The model generator 112 can generate a model for each target anatomy within the image data sets 134, and each fiducial marker within the image data sets 134. For example, the model generator 112 can generate a model for the patient's spine (the fiducial marker) and the patient's heart (the anatomical target).

In some implementations, the model generator 112 can segment the image data sets 134 by processing each slice 500 of the CT image or MR images included in the image data sets 134. For example, the model generator 112 can binarize each slice 500 of the image data set 134 at a predetermined threshold value according to the target anatomical structure being segmented. In some implementations, the threshold value can be manually set or tuned by using the mean value of the pixel intensities of target anatomical structures and background images (e.g., bone vs. soft tissue background). Binarizing each slice 500 can generate a rough segmentation that can include many isolated 3D objects due. To remove the noise, the model generator 112 can only the objects with a size above a predetermined threshold. The model generator 112 can fill the inner holes of the selected objects to generate the 3D model. The process can be repeated for each slice 500 to identify the object within each slice 500. The model generator 112 can combine each portion identified in each of the slices 500 to generate a reconstructed 3D model 502 of the object. The model generator 112 can perform post-processing on the reconstructed 3D model 502. For example, the model generator 112 can smooth the outer edges of the reconstructed 3D model 502. In some implementations, the post-processing can include refinement or segmentation of the reconstructed model 502. For example, the model generator 112 can remove non-target anatomies, such as the ribs, chest bones, and small peripheral blood vessels from the reconstructed model. The model generator 112 can segment the reconstructed model 502. For example, the model generator 112 can segment the spine and heart into separate models. The model generator 112 can, for example, save the reconstructed model 500 to the database 122 as the model of the spine 124 and the model of the target 126. In some implementations, the model generator 112 can save the model of the spine 124 and the model of the target 126 to the database 122 as a model 502.

Figure 6:
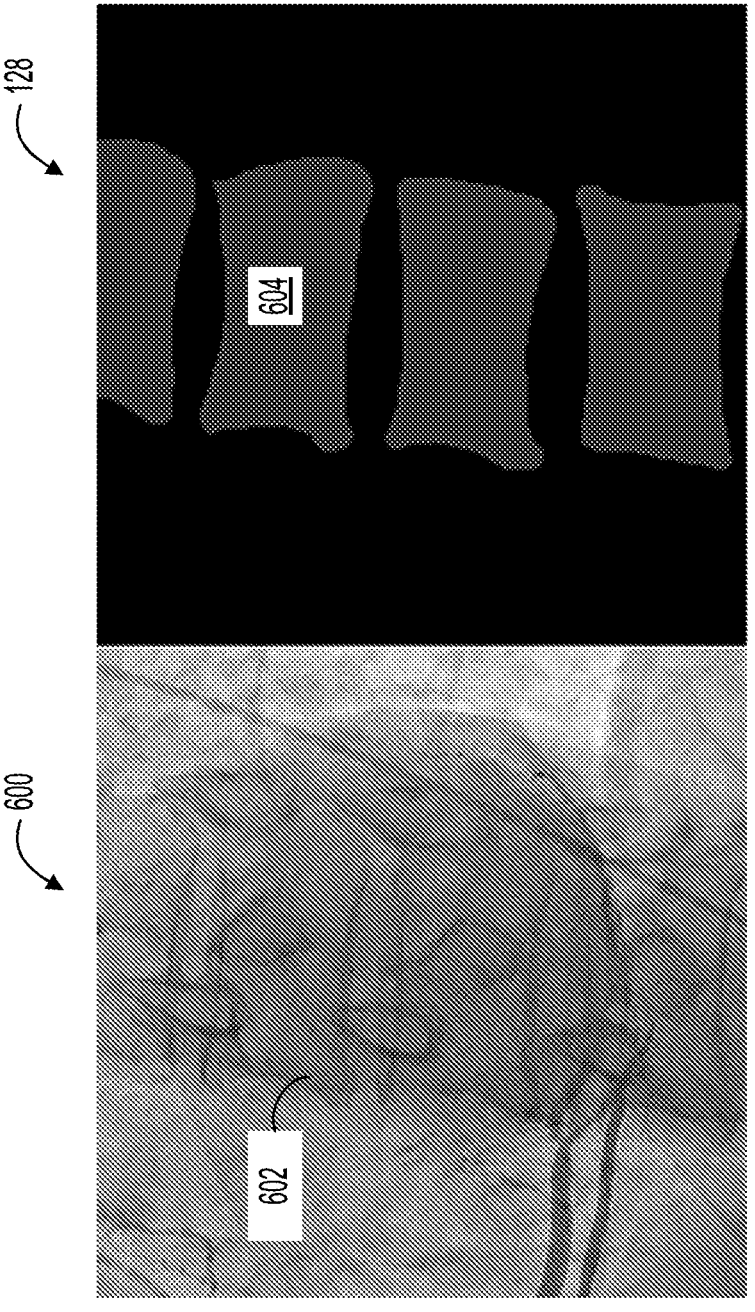
FIG. 6 illustrates the process of segmenting a fluoroscopic image using the system illustrated in FIG. 1.

FIG. 6 illustrates the process of segmenting a fluoroscopic image. FIG. 6 illustrates a fluoroscopic image 600 and mask of the spine 128. The fluoroscopic image 600 can be an example of an image data set 134 from the second imaging device 106. The segmentation engine 114 can segment the spine from the fluoroscopic image 600 to use the spine as a universal fiducial marker between the image data sets 134 received from the first imaging device 104 and the second imaging device 106. The guidance system 102 can use the spine as a universal fiduciary marker because the spine can be relatively clear in both imaging modalities of the first imaging device 104 and the second imaging device 106 and the spine is stable during imaging (e.g., e.g., introduced little movement artifacts), and is stable between from a pre-operative to operative time. The segmentation engine 114 can identify the vertebrae 602 in the fluoroscopic image 600 and generate the mask of the spine 128 that includes segments 604 indicating the location of the vertebrae in the fluoroscopic image 600.

To segment the spine from the fluoroscopic image 600, the segmentation engine 114 can pre-process the fluoroscopic image 600. For example, the segmentation engine 114 can remove noise or other artifacts in the fluoroscopic image 600 by soothing the fluoroscopic image 600. The segmentation engine 114 can smooth the fluoroscopic image 600 with, for example, Gaussian smoothing. The segmentation engine 114 can binarize the fluoroscopic image 600 to detect objects (e.g., the vertebrae) within the fluoroscopic image 600. The segmentation engine 114 can apply a bounding box around the identified objects and then binarize the portion of the fluoroscopic image 600 within the bounding box.

In some implementations, the segmentation engine 114 can segment the universal fiducial marker and medical device from the fluoroscopic image 600 with a machine learning algorithm. For example, the segmentation engine 114 can include a convolutional neural network. The convolutional neural network can be trained with pre-segmented fluoroscopic images 600 that identify the universal fiducial marker (e.g., the spine) and the medical device (e.g., a catheter). The convolutional neural network can receive the fluoroscopic image 600 and process the fluoroscopic image 600 to identify the universal fiducial marker and generate a mask identifying the location of the universal fiducial marker in the fluoroscopic image 600. The convolutional neural network can also process the fluoroscopic image 600 to identify the medical device and generate a mask identifying the location of the medical device in the fluoroscopic image 600. In some implementations, the segmentation engine 114 can include a first convolutional neural network that identifies the universal fiducial marker and a second convolutional neural network that identifies the medical device.

In some implementations, the segmentation engine 114 can determine the position of the medical device's position in a 3D space once the medical device is segmented. To determine the position in the 3D space, the segmentation engine 114 can segment or otherwise identify the medical device in two fluoroscopic images. The two fluoroscopic images can be captured from two different angles. For example, each of the fluoroscopic images can be captured from one of a left anterior oblique (LOA) angle, right anterior oblique (RAO) angle, or anterior-posterior (AP) angle. The images can also include cranial or caudal angulation. The fluoroscopic images can be captured at an angle between about 0° and about 90°, between about 10° and about 90°, between about 15° and about 90°, between about 15° and about 75°, between about 30° and about 75°, or between about 45° and about 75° left or right of the AP plane. The second imaging device 106 can include the angle of image capture in the fluoroscopic image as metadata. The segmentation engine 114 can relate positions in each of the fluoroscopic images by:

$$P_1 = \begin{bmatrix} x_1 \\ y_1 \\ z_1 \end{bmatrix} T_{3d} \cdot P_2 = \begin{bmatrix} \cos\theta & 0 & \sin\theta \\ 0 & 1 & 0 \\ -\sin\theta & 0 & \cos\theta \end{bmatrix} \begin{bmatrix} x_2 \\ y_2 \\ z_2 \end{bmatrix}$$

where $P_1$ and $P_2$ are the catheter's position in each of the two images, and $\theta$ the is the rotation angle between the two images. The above equation can be solved for $z_1$ and $z_2$ to provide a 3D position for the catheter.

FIGS. 7A-7F illustrate the process for detecting the medical device in an image data set 134. FIG. 7A illustrates an example image data set 134, which is a fluoroscopic image that includes the spine 700 and a catheter 702. The segmentation engine 114 can identify the location of the catheter 702 and segment the catheter 702. The segmentation engine 114 can identify the point where the catheter 702 enters the frame of the image data set 134 and set a region of interest at the location where the catheter 702 enters the frame. FIG. 7B illustrates the region of interest 704. The segmentation engine 114 can identify the edges of the catheter 702. For example, the segmentation engine 114 can calculate a gradient of the region of interest 704. FIG. 7C illustrates the gradient 706 of the region of interest 704. FIG. 7D illustrates the derivative of the values of the pixels along a row of the gradient 706. The segmentation engine 114 can identify the peaks 708 in each row of the gradient 706. The peaks 708 can correspond to an edge of the catheter 702. The segmentation engine 114 can identify a center line of the catheter 702 as halfway between the two peaks 708 (or edges of the catheter 702). The segmentation engine 114 can advance the region of interest 704 to a second location. For example, the segmentation engine 114 can move the region of interest 704 to the end of the center line 710. The segmentation engine 114 can continue to identify the edges of the catheter 702 and generate a center line 701 until the region of interest 704 reaches the end of the catheter 702. FIG. 7F illustrates the center line 710 extending along the full length of the catheter 702 within the image data set 134.

Figures 8A, 8B, 8C, 8D, 8E:
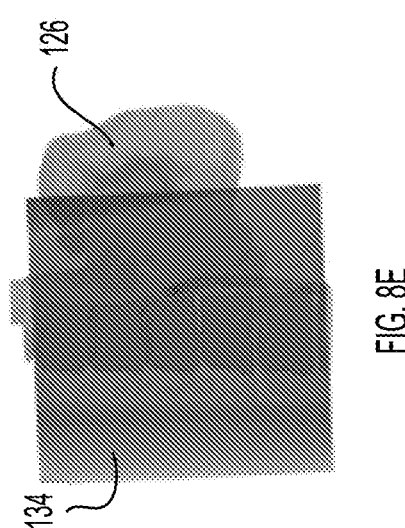
FIGS. 8A-8E illustrate the alignment of a fluoroscopic image with models of anatomical structures using the system illustrated in FIG. 1.

FIGS. 8A-8E illustrate the alignment of a fluoroscopic image with models of anatomical structures. FIG. 8A illustrates an image data set 134 that is a fluoroscopic image. FIG. 8B illustrates a mask of the spine 128 generated from the fluoroscopic image illustrated in FIG. 8A. As described above, the segmentation engine 114 can segment the fluoroscopic image to generate the mask of the spine 128. FIG. 8C illustrates an example model of the spine 124 and an example model of the target 126 from the same subject from which the fluoroscopic image of FIG. 8A was captured. As illustrated in FIG. 8C, the model of the spine 124 and the model of the target 126 exist in a 3D volume. The model of the spine 124 and the model of the target 126 can be viewed from an angle to generate a 2D projection 800. The 2D projection 800 is the view of the model of the spine 124 or the model of the target 126 from the angle. FIG. 8D illustrates the 2D projection 800 of the model of the spine 124 from the angle illustrated in FIG. 8C.

Since the spine is a rigid object and its relative position inside the subject is consistent, the spine can be used to determine the transformation matrix between the fluoroscopic images (of FIG. 8A) and the model of the target 126. The registration engine 116 can use the 2D projection 800 of the model of the spine 124 as the fixed reference image ($I_c$)

and the fluoroscopic images captured at the same angle can be used as the moving image ($I_f$). The registration engine 116 can register the two image modalities to calculate a transform matrix, $T_f$, such that the display generator 120 can place the medical device and the model of the target 126 into a single coordinate system with the scaling factor k, rotation angle ($\theta$), and translation ($t_x, t_y$).

$$P = \begin{bmatrix} x_c \\ y_c \\ 1 \end{bmatrix} = T_f P_f = \begin{bmatrix} k\cos(\alpha) & k\sin(\alpha) & t_x \\ k\sin(\alpha) & k\cos(\alpha) & t_y \\ 0 & 0 & 1 \end{bmatrix} \begin{bmatrix} x_f \\ y_f \\ 1 \end{bmatrix}$$

where, $P_c$ and $P_f$ are the spine positions in the CT and fluoroscopic images, respectively. In order to decouple the scale, rotation and translation factors, the spine images are first processed through 2D Fourier transformation. The transformed images $F_c$ and $F_{the}$ are related by $$F_c(x,y)=e^{-j\Phi(v,v)}k^{-2}F_f[k^{-1}(u\cos\alpha+v\sin\alpha),k^{-1}(-u\sin\alpha+v\cos\alpha)]$$

where $\Phi$ (u,v) is the spectral phase change depending on scaling, rotation, and translation. The spectral amplitude relationship:

$$F_c(x,y)=k^{-2}|F_f[k^{-1}(u\cos\alpha+v\sin\alpha),k^{-1}(-u\sin\alpha+v\cos\alpha)]|$$

indicates that the rotation of the spine results in the same rotation by the same angle in the spectral amplitude images and the scaling by k scales the spectral amplitude by k−1. The rotation and scaling can be further decoupled by defining the spectral amplitudes in the polar coordinates ($\theta,\rho$), such that the above equation can be expressed as:

$$PL_c(\theta,\rho)=k^{-2}PL_f(\theta-\alpha,\rho/k)$$

The image rotation $\alpha$ is then converted as the shift along the angular axis. The scaling of the original image is converted to a scaling of the radial coordinate (i.e., $\rho/k$). By using a logarithmic scale for the radial coordinate, the scaling is then converted to a translation:

$$L_c(\theta,\gamma)=k^{-2}L_f(\theta-\alpha,\gamma-k)$$

where, $\gamma=\log(\rho)$ and $\kappa=\log(k)$. Using the polar logarithmic representation, both rotation and translation can be converted to the translations. Through Fourier transforming the polar-logarithmic representations provides:

$$FL_c(\chi,\psi)=k^{-2}e^{-j2\pi(\chi\alpha+\psi k)}FL_f(\chi,\psi)$$

where rotation and scaling are represented as phase correlations $e^{-j2\pi(\chi\alpha+\psi\kappa)}$. In the ideal case when two identical images are correlated only with the translation, the inverse Fourier transform of the phase shifts is a Dirac $\delta$-function at ($\alpha,\kappa$). In real cases, the rotation and scaling factors are determined by finding the maximum location from the inverse Fourier transformation image. With the same scale and rotation, the phase correlation method is used again to determine the translation factor ($t_x$, $t_y$). The combination of the Fourier and polar-logarithmic transformation is also called Fourier-Mellin method.

In some implementations, the registration engine 116 can include a machine learning algorithm to register the fluoroscopic images and the models of the universal fiducial marker and anatomical target. For example, the registration engine 116 can generate a plurality of 2D projections captured from a plurality of different angles. The registration engine 116 can include a machine learning algorithm, such as a convolutional neural network, that can determine if the universal fiducial marker from the 2D projection 800 matches the mask of the spine 128. The registration engine 116 can determine the plurality of different angles based on the angle indicated in the metadata of the fluoroscopic image. For example, if the metadata indicates that the fluoroscopic image was captured at 30°, the registration engine 116 can generate a 2D projection 800 at every angle between 25° and 35°. The registration engine 116 can generate 2D projections 800 at angles at and around the angle indicated by the metadata of the fluoroscopic image because the subject may be rotated with respect to the second imaging device 106 such that the angle indicated by the metadata is not the actual angle of the subject with the fluoroscopic image is captured.

Figure 9:
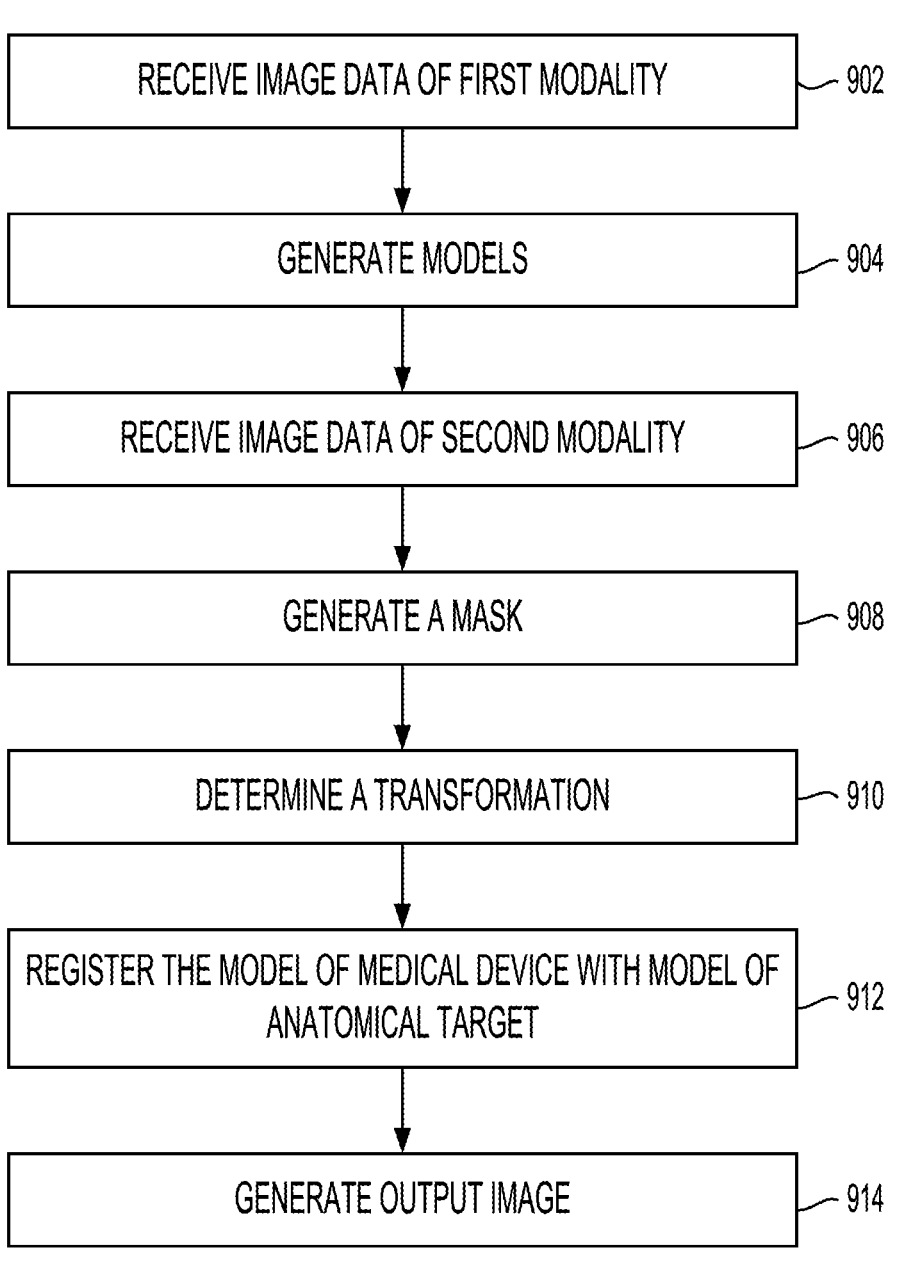
FIG. 9 illustrates a block diagram of an example method of performing image guidance using the system illustrated in FIG. 1.

FIG. 9 illustrates a block diagram of an example method 900 of performing image guidance. The method 900 can include receiving image data of a first modality (BLOCK 902). The method 900 can include generating models from the received image data (BLOCK 904). The method 900 can include receiving image data of a second modality (BLOCK 906). The method 900 can include generating one or more masks (BLOCK 908). The method 900 can include determining a transformation (BLOCK 910). The method 900 can include registering the models based on the transformation (BLOCK 912). The method 900 can include generating an output image (BLOCK 914).

As set forth above, the method 900 can include receiving image data (BLOCK 902). Also referring to FIG. 1, among others, the guidance system 102 can receive the image data as a first image data set 134 from the first imaging device 104. The image data set 134 can include image data of a first imaging modality. For example, the first imaging device 104 can be a CT imager or an MR imager. The image data set 134 can include a plurality of image or slices captured pre-operatively of the patient. The first image data set 134 can include a universal fiducial marker and the anatomical target. For example, the first image data set 134 can include the spine as the universal fiducial marker and the heart as the anatomical target.

The method 900 can include generating models from the received image data (BLOCK 904). The model generator 112 can generate 3D models of the universal fiducial marker and the anatomical target based on the first image data set 134. For example, the database 122 can generate a model of the spine (e.g., universal fiducial marker) and the heart (e.g., the anatomical target). As described above, the model generator 112 can segment the universal fiducial marker, and the anatomical target from the first image data sets 134. The model generator 112 can store the models in the database 122 as the model of the spine 124 and the model of the target 126. The model generator 112 can generate the models of the universal fiducial marker and the anatomical target in the same coordinate system or 3D space. The coordinate system of the models can be referred to as a first coordinate system.

The method 900 can include receiving image data of a second imaging modality (BLOCK 906). The image data of the second imaging modality can be generated during an operation or procedure when the medical device is positioned within a subject. For example, the second imaging device 106 can capture the image data of the second imaging modality during a cardiac procedure when a catheter is being advanced toward a subject's heart. The guidance system 102 can receive the image data as a second set of image data sets 134. The second image data set 134 can include fluoroscopic images. The second image data set 134 can include the universal fiducial marker and a medical device. The universal fiducial marker captured in the second image data set 134 can be the same universal fiducial marker captured in the first image data set 134 of BLOCK 902. For example, the second image data set 134 can be fluoroscopic images that can include the spine (e.g., the universal fiducial marker) and a catheter (e.g., the medical device). The second image data set 134 can include images captured at a plurality of angles. For example, the second imaging device 106 can be a fluoroscopic imager that can capture fluoroscopic images at a left anterior oblique (LOA), right anterior oblique (RAO), anterior-posterior (AP). The images can include cranial or caudal angulation. For example, the fluoroscopic images can be captured at an angle between about 0° and about 90°, between about 10° and about 90°, between about 15° and about 90°, between about 15° and about 75°, between about 30° and about 75°, or between about 45° and about 75° left or right of the AP plane.

The method 900 can include generating a mask (BLOCK 908). The segmentation engine 114 can generate one or more masks from the second image data set 134. For example, the segmentation engine 114 can generate a mask for the spine and a mask of the medical device from the fluoroscopic images. The masks can be bit masks that can indicate the location of the spine or medical device in the fluoroscopic images. The mask of the spine or the medical device can have a second coordinate system. The guidance system 102 can determine a location of the medical device with respect to a coordinate system of the second image data sets 134. For example, the second image data sets 134 can be 2D images that the second imaging device 106 can capture at different angles with respect to the subject. As described above, based on the angle between two images, the guidance system 102 can determine a 3D location of the medical device in a second coordinate system.

The method 900 can include determining a transformation (BLOCK 910). The transformation can transform coordinate positions of the second coordinate system (associated with, for example, fluoroscopic images) to coordinate positions of the first coordinate system (associated with, for example, the models). The transformation can be a transformation matrix that can include scaling factors, rotation factors, and translation factors for transforming a position from the second coordinate system to a position of the first coordinate system. Having calculated a position of the medical device in the first coordinate system, the guidance system 102 can calculate, based on the transformation, a position of the medical device in the second coordinate system.

The method 900 can include registering the models based on the transformation (BLOCK 912). The registration engine 116 registers the location of the medical device from the 3D location determined from the second image data set 134 (e.g., the fluoroscopic images) to the coordinate system of the model of the spine 124 and the model of the target 126. The guidance system 102 can generate a model of the medical device based on the determined position of the medical device in the first coordinate system. The guidance system 102 can load the model of the medical device, positioned in the first coordinate system, into a 3D volume defined in the first coordinate system. The guidance system 102 can load into the same 3D volume, the model of the anatomical target. As the model of the medical device location is determined based on a real-time image of the medical device, the combined 3D volume with the model of the medical device and the anatomical target illustrates the real-time position of the medical device with respect to the model of the anatomical target.

The method 900 can include generating an output image (BLOCK 914). The display generator 120 can generate an output image. The output image can be a 2D image. For example, the display generator 120 can project the co-registered 3D models to a 2D projection plane and output the 2D projection plane as the 2D image. In some implementations, the output image can be a 3D image. The display generator 120 can receive input from a user to enable a user to manipulate the 3D image. For example, the user can provide inputs to spin, zoom, rotate, move, or transect portions of the models in the 3D image.

Figure 10:
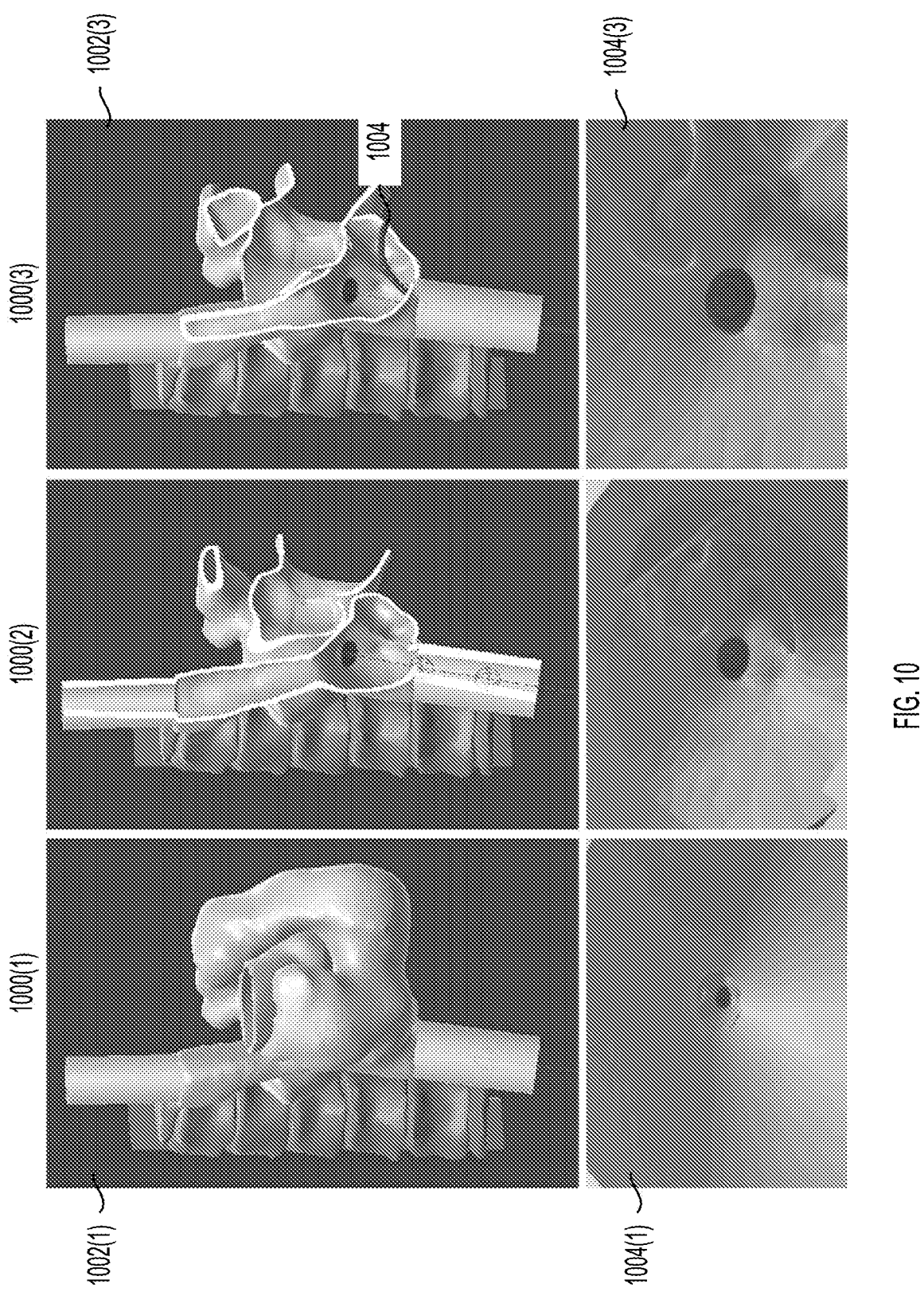
FIG. 10 illustrates a plurality of output images generated using the system illustrated in FIG. 1.

FIG. 10 illustrates a plurality of output images 1000(1)-1000(3), which can generally be referred to as the output images 1000. The output images 1000 can include a rendering of the models 1002(1)-1002(3), which can generally be referred to as the rendering of the models 1002. The rendering of the models can include a rendering of the model of the spine 124, a rendering of the model of the target 126, and a rendering of the medical device 1004. Each of the models in the rendering of the models 1002 are co-registered into the same coordinate system. The output images 1000 can include a secondary view 1006(1)-1006(3), which can be generally be referred to as a secondary view 1006. As illustrated in FIG. 10, the secondary view 1006 can include a first-person view from the catheter. The secondary view 1006 can include operational information, such as the medical device's distance to the target.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A method of image guidance, comprising:
   receiving a first image data set comprising a rigid anatomical structure serving as a fiducial marker of a subject and an anatomical target comprising a target tissue;
   segmenting the first image data set to identify the rigid anatomical structure and the target tissue and to generate a three-dimensional (3D) model of the rigid anatomical structure and the target tissue;
   receiving at least one fluoroscopic image comprising the rigid anatomical structure and a medical device comprising a radiopaque marker, the at least one fluoroscopic image being acquired or selected at a physiological phase of the subject that was present during acquisition of the first image data set;

applying a segmentation engine comprising a first machine learning model to the at least one fluoroscopic image to generate a mask of the rigid anatomical structure in the at least one fluoroscopic image, the mask identifying indicating a location of the rigid anatomical structure in the at least one fluoroscopic image;
providing the mask and a projection of the 3D model to a registration engine comprising a second machine learning model trained on pairs of masks and projections with known transformation parameters, the registration engine providing a registration transformation that aligns the mask of the rigid anatomical structure with the projection of the 3D model, the registration transformation being refined by determining at least one of a rotation angle, a translation, or a scaling factor based on a projection of the radiopaque marker in the at least one fluoroscopic image; and
generating a three-dimensional (3D) rendering of the medical device registered with a geometry of the target tissue for intra-procedural guidance.

2. The method of claim 1, wherein the first image data set comprises preoperative images.

3. The method of claim 1, wherein the first machine learning model comprises a convolutional neural network trained with pre-segmented fluoroscopic images to identify a spine and the medical device.

4. The method of claim 1, further comprising generating a second mask of the medical device from the at least one fluoroscopic image.

5. The method of claim 1, wherein receiving the at least one fluoroscopic images comprises receiving a first fluoroscopic image captured at a first angle and a second fluoroscopic image captured at a second angle.

6. The method of claim 1, wherein the first image data set comprises computed tomography (CT) images or magnetic resonance (MR) images.

7. The method of claim 1, wherein the anatomical target is a heart.

8. The method of claim 1, wherein the medical device is a catheter comprising the radiopaque marker.

9. The method of claim 8, further comprising determining at least one of a rotation angle, a translation, or a scaling factor based on a projection of the radiopaque marker in the at least one fluoroscopic image.

10. The method of claim 1, further comprising correcting for a periodic motion of the subject.

11. The method of claim 10, wherein correcting for the motion of the subject comprises identifying portions of one or more fluoroscopic images captured during a same portion of the periodic motion as in the first image data set.

12. The method of claim 1, further comprising generating a two-dimensional (2D) image showing a real-time position of the medical device in relation to the anatomical target.

13. The method of claim 1, further comprising displaying the 3D rendering using an augmented reality headset.

14. A system for image guidance, comprising a memory storing processor executable instructions and one or more processors to:
   receive a first image data set comprising a rigid anatomical structure serving as a fiducial marker of a subject and an anatomical target comprising a target tissue;
   segment the first image data set to identify the rigid anatomical structure and the target tissue and to generate a three-dimensional (3D) model of the rigid anatomical structure and the target tissue;

receive at least one fluoroscopic image comprising the rigid anatomical structure and a medical device comprising a radiopaque marker, the at least one fluoroscopic image being acquired or selected at a physiological phase of the subject that was present during acquisition of the first image data set;

apply a segmentation engine comprising a first machine learning model to the at least one fluoroscopic image to generate a mask of the rigid anatomical structure in the at least one fluoroscopic image, the mask indicating a location of the rigid anatomical structure in the at least one fluoroscopic image;

provide the mask and a projection of the 3D model to a registration engine comprising a second machine learning model trained on pairs of masks and projections with known transformation parameters, the registration engine providing a registration transformation that aligns the mask of the rigid anatomical structure with the projection of the 3D model, the registration transformation being refined by determining at least one of a rotation angle, a translation, or a scaling factor based on a projection of the radiopaque marker in the at least one fluoroscopic image; and generate a 3D rendering of the medical device registered with a geometry of the anatomical target comprising the target tissue for intra-procedural guidance.

15. The system of claim 14, wherein the first image data set comprises preoperative images.

16. The system of claim 14, wherein the first machine learning model comprises a convolutional neural network trained with pre-segmented fluoroscopic images to identify a spine and the medical device.

17. The system of claim 14, further comprising the one or more processors to generate a second mask of the medical device from the at least one fluoroscopic image.

18. The system of claim 14, further comprising the one or more processors to receive a first fluoroscopic image captured at a first angle and a second fluoroscopic image captured at a second angle.

19. The system of claim 14, wherein the first image data set comprises computed tomography (CT) images or magnetic resonance (MR) images.

20. The system of claim 14, wherein the medical device is a catheter comprising the radiopaque marker, and wherein the system further comprises the one or more processors to determine at least one of a rotation angle, a translation, or a scaling factor based on a projection of the radiopaque marker in the at least one fluoroscopic image.

\* \* \* \* \*